(12) United States Patent  (10) Patent No.: US 6,893,468 B2
Lund  (45) Date of Patent: May 17, 2005

(54) ABOVE AND BELOW KNEE PROSTHESIS—LEG COUPLER

(76) Inventor: Arnold A. Lund, 18363 Applegate Rd., Applegate, CA (US) 95703

( * ) Notice: Subject to any disclaimer, the term of this patent is extended or adjusted under 35 U.S.C. 154(b) by 0 days.

(21) Appl. No.: 10/170,877

(22) Filed: Jun. 12, 2002

(65) Prior Publication Data

US 2003/0233151 A1 Dec. 18, 2003

(51) Int. Cl.$^7$ .................................................. A61F 2/80
(52) U.S. Cl. .......................................... 623/36; 623/33
(58) Field of Search .............................. 623/36, 38, 33; 403/324–325; 292/303, 306, 305, 327

(56) References Cited

U.S. PATENT DOCUMENTS

| | | | | |
|---|---|---|---|---|
| 5,116,382 A | * | 5/1992 | Steinkamp et al. | 623/38 |
| 5,226,918 A | * | 7/1993 | Silagy et al. | 623/32 |
| 5,507,834 A | * | 4/1996 | Laghi | 623/36 |
| 5,759,206 A | * | 6/1998 | Bassett | 623/27 |
| 5,888,234 A | * | 3/1999 | Littig | 623/38 |
| 6,051,026 A | * | 4/2000 | Biedermann et al. | 623/38 |
| 6,106,559 A | * | 8/2000 | Meyer | 623/33 |
| 6,235,062 B1 | * | 5/2001 | Gramnas | 623/33 |
| 6,334,876 B1 | * | 1/2002 | Perkins | 623/34 |
| 6,361,569 B1 | * | 3/2002 | Slemker et al. | 623/33 |
| 6,402,789 B1 | * | 6/2002 | Gramnas | 623/38 |
| 6,511,513 B1 | * | 1/2003 | Laghi | 623/33 |
| 2003/0195636 A1 | * | 10/2003 | Coop | 623/36 |

* cited by examiner

*Primary Examiner*—Alvin Stewart
(74) *Attorney, Agent, or Firm*—Mark C. Jacobs

(57) ABSTRACT

A device to couple a prosthesis to a human leg stump above-the-knee in a first embodiment, and below the knee in the second embodiment. The device has an upper and a lower plate, the connecting mechanism being disposed in the lower plate. The upper plate is round and the same in both embodiments, but for above-the-knee junctions, the lower plate is elliptical while for below-the-knee junctions, the lower plate is round and of the same diameter as the upper plate. The operative connection is achieved by use of a guillotine, whose horizontally disposed blade engages one of a plurality of grooves on a locking stud. The movement of the spring-loaded guillotine is controlled by a retractable release pin to permit the guillotine to engage in or disengage the groove to which is disposed.

15 Claims, 7 Drawing Sheets

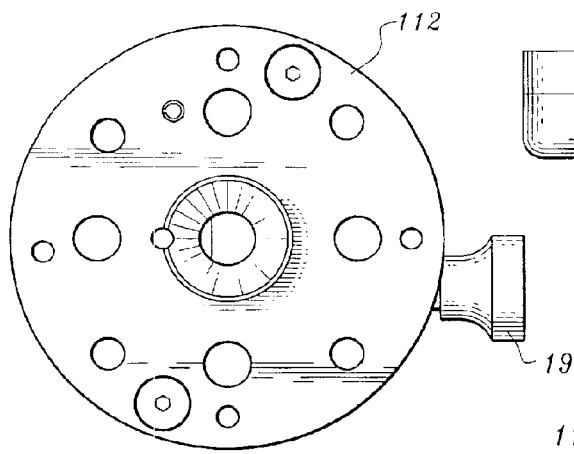
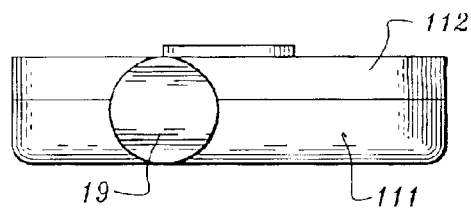
Fig. 8
Fig. 9
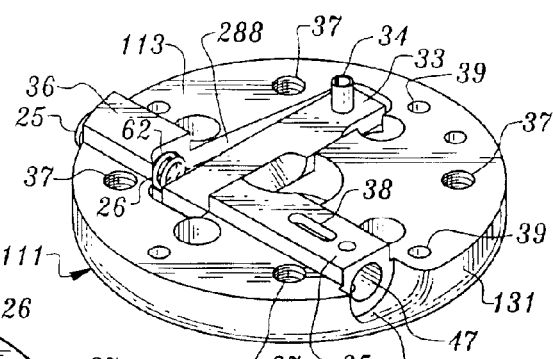
Fig. 10
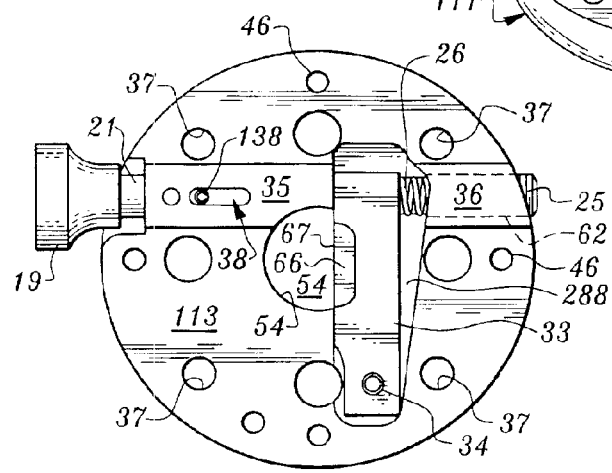
Fig. 11
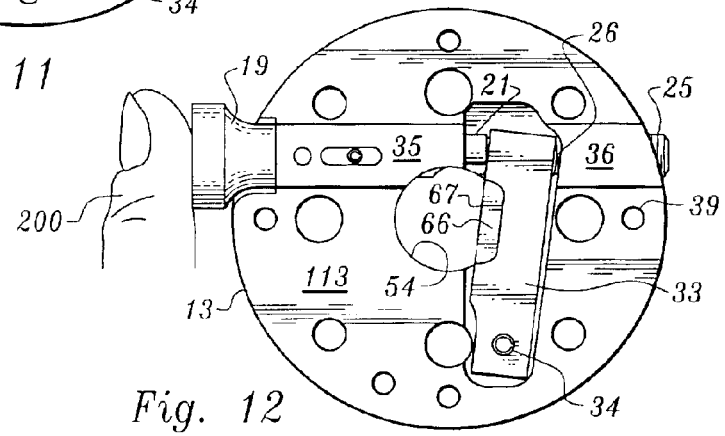
Fig. 12

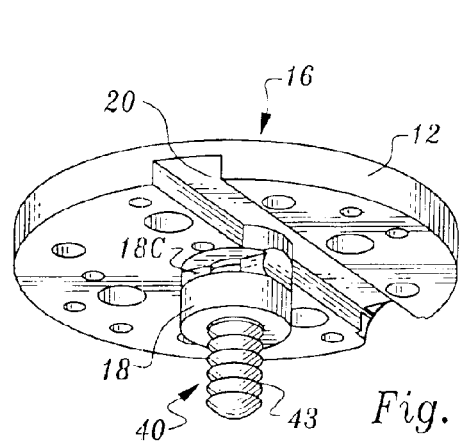
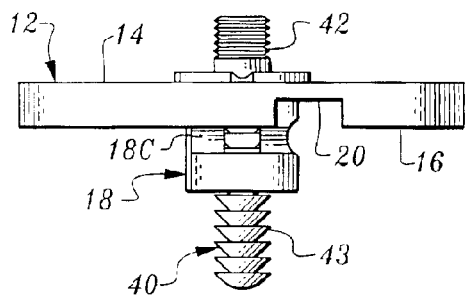
Fig. 13
Fig. 14
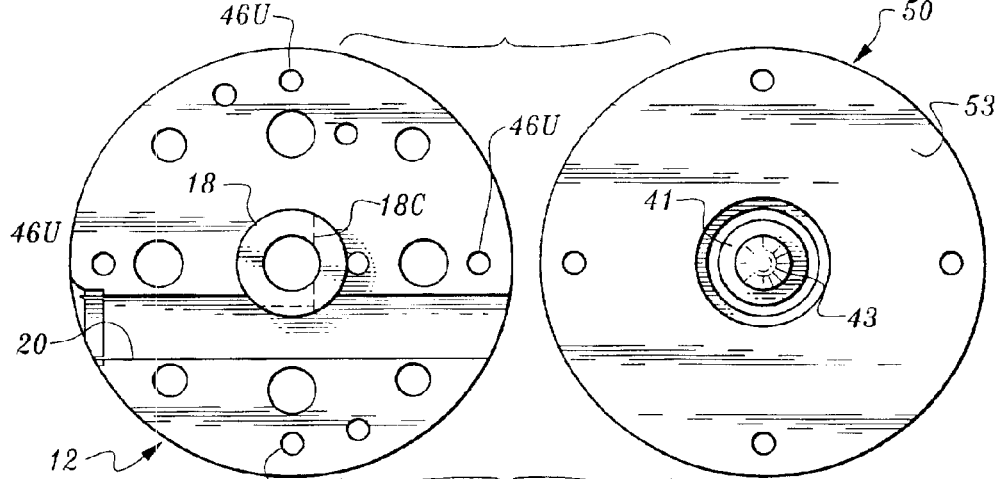
Fig. 15
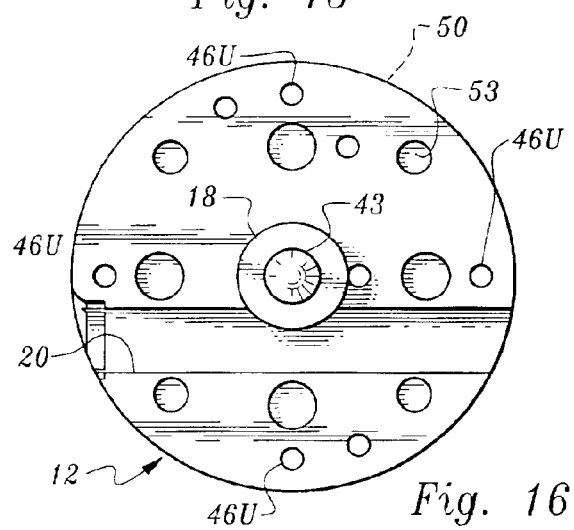
Fig. 16

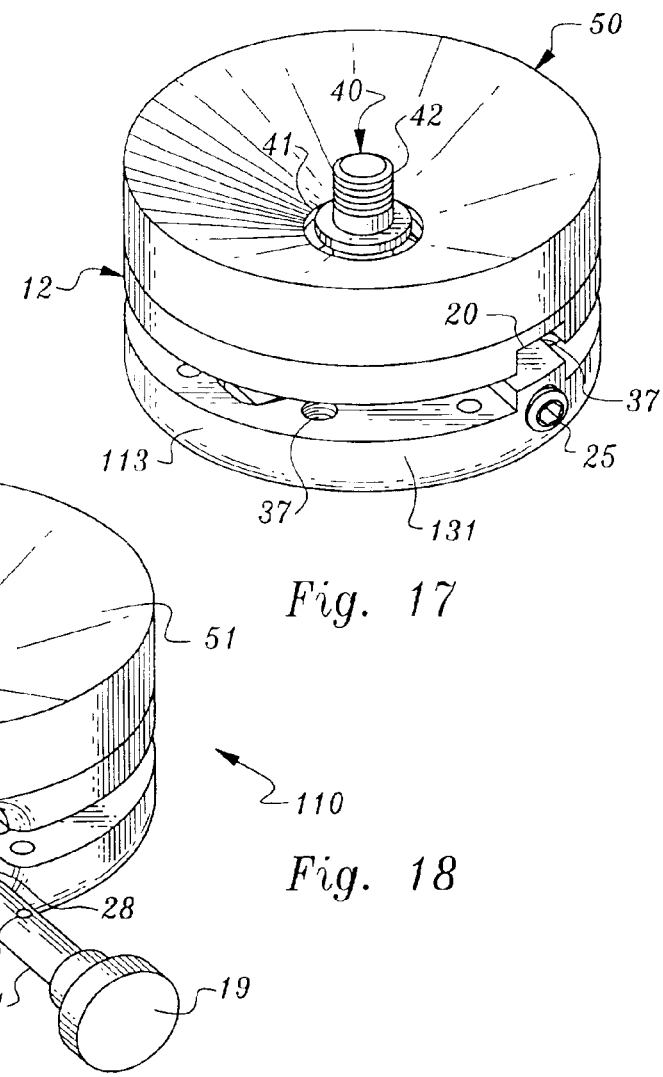
Fig. 17
Fig. 18
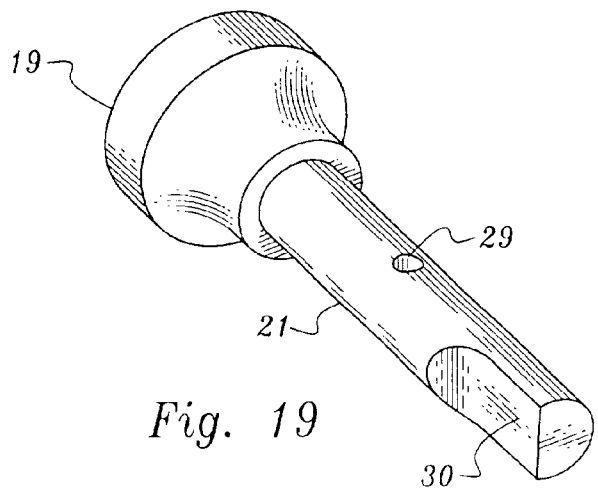
Fig. 19

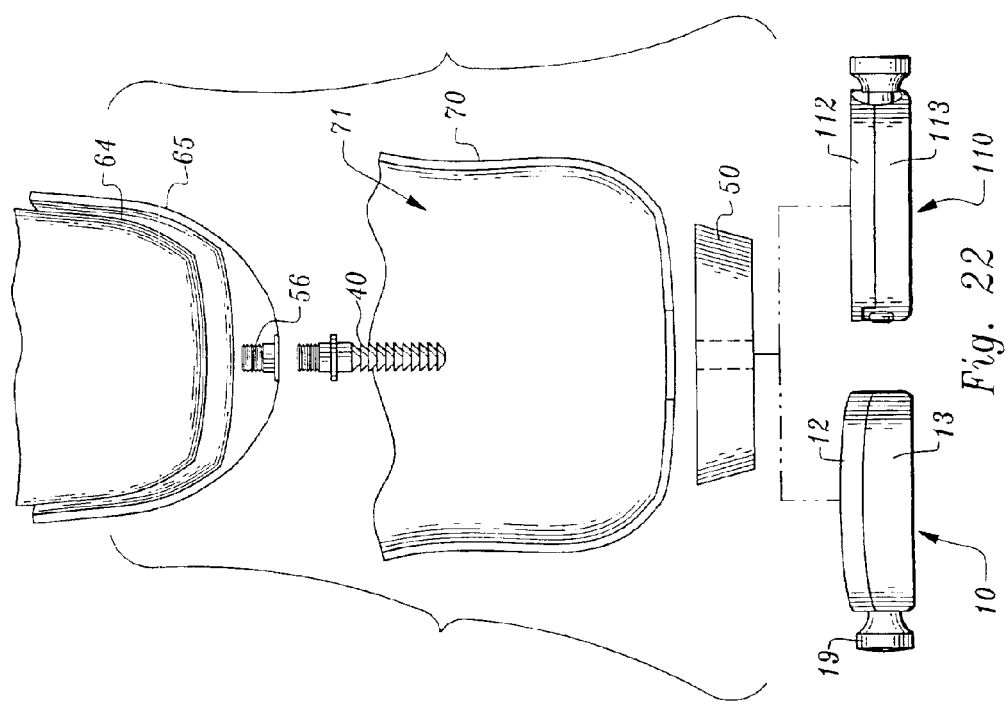
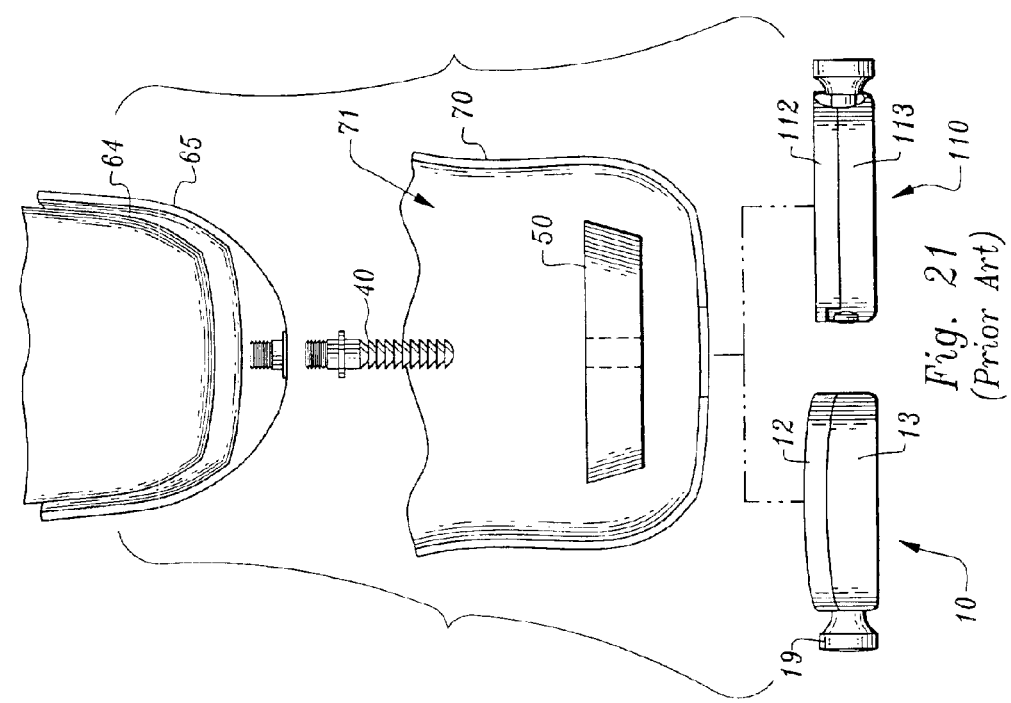

ABOVE AND BELOW KNEE PROSTHESIS— LEG COUPLER

FIELD OF THE INVENTION

This invention relates to prosthetic devices and more particularly to a coupler which in one embodiment is used above-the-knee and in the second embodiment is used below-the-knee to connect the leg stump disposed within a liner and sleeve to the prosthesis.

BACKGROUND OF THE INVENTION

This invention relates to an improved coupler for releasably connecting a prosthetic device in the form of an artificial leg to a sleeve which receives the stump of an amputee's limb. A locking stud, engages both the sleeve and the prosthesis through the interposed attachment coupler. The coupler of this invention uses a retractable release pin or guillotine which engages one of a plurality of grooves formed within the locking stud and which is projecting from the sleeve holding the leg stump of the user.

In the past there have been several patented inventions that relate to below-the-knee prosthesis couplers. All of these incorporate some type of release pin to disengage the locking stud or stud lock from the coupler.

One of the problems associated with certain couplers is that the body must become integral and permanently molded into the prosthetic socket during fabrication. If the cylindrical body is improperly positioned during fabrication, the pin may not align easily and consistently with the coupler latching mechanism.

Other couplers require the use of a cupped flange or pin guide that mounts permanently within the socket. The coupler of this invention, on the other hand, uses a cupped flange or pin guide that can be mounted external to the sleeve, and is removable from the socket.

The cupped flange of this invention can be used easily adjacent to or spaced from the coupler of this invention. The coupler includes a plurality of screws to secure the lower plate thereof to the upper plate. Such screws also connect the pin guide or cupped-shaped flange to the upper plate body section.

It is seen therefore that there exist a need for a new and improved coupler for both below and above-the-knee prosthesis junction.

SUMMARY OF THE INVENTION

The current invention is directed to an improved coupler for releasably connecting a prosthetic leg to a sleeve configured to receive a stump of an amputee. A locking stud serves as the connecting means between the sleeve and the coupler. A pin guide or cupped flange can be used exteriorly of the sleeve with the coupler of this invention. The coupler has an upper plate and a lower plate, and each formed preferably of metal or rigid plastic. The choice of configuration of the upper plate mandates the location of use for the coupler. If the top surface of the upper plate is disposed angularly rather than parallel to the bottom surface, the coupler is intended for use in an above-the-knee junction of the amputee's stump to the prosthesis. But if the top surface is parallel to the bottom surface thereof, the coupler is intended for use in the below-the-knee junction.

A release pin is used to disengage a guillotine-type mechanism from engagement of one of a plurality of grooves formed on the locking stud that projects from the sleeve holding the wearer's stump.

Known prior art.

The device of this invention is seen to be an improvement over the structures of Litig as disclosed and claimed in U.S. Pat. No. 5,888,234, issued Mar. 30, 1999, and Meyer U.S. Pat. No. 6,106,559, issued Aug. 22, 2000. Other features and advantages will be readily apparent from the description, drawings, and the claims found herein.

This invention pertains to a coupler for both below and above-the-knee prosthesis junctions which device eliminates the problem of the prior art. The device is easy to fabricate and install.

The invention accordingly comprises the device possessing the features, properties, the selection of components which are amplified in the following detailed disclosure, and the scope of the application of which will be indicated in the appended claims.

For a fuller understanding of the nature and objects of the invention, reference should be made to the following detailed description, taken in conjunction with the accompanying drawings.

Other objects of the invention will in part be obvious and will in part appear hereinafter.

BRIEF DESCRIPTION OF FIGURES

FIG. 8 is a top plan view of the second embodiment of this invention.

FIG. 9 is a side elevational view of the second embodiment.

FIG. 10 is a top perspective view of the lower plate used in the second embodiment of this invention, and its internal elements without the stud reciever.

FIG. 11 is a top plan view of the lower plate of the second embodiment with the locking guillotine in it's at rest position, to lock the stud.

FIG. 12 is a top plan view of the lower plate shown in FIG. 16 with the locking guillotine in it activated (stud release) position.

FIG. 13 is a bottom perspective view of the upper plate and the locking stud and stud receiver.

FIG. 14 is an elevational view of the components in FIG. 10 with the stud receiver.

FIG. 15 is a perspective view of the underside of the top plate of the second embodiment and the underside of the cupped flange with the locking stud disposed therein.

FIG. 16 is a plan view of the underside of the top plate of the second embodiment over the cupped flange.

FIG. 17 is a rear partially exploded view showing the second embodiment with a cupped flange attached to the upper plate.

FIG. 18 is a front perspective view of the elements shown in figures along with the handled release pin.

FIG. 19 is a perspective view of the handled release pin of this invention.

FIG. 21 is a diagrammatic elevational view illustrating the attachment of the coupler of this invention to the leg stump of the wearer of the prosthesis, utilizing prior art procedures and relationship of parts, and prior art pin guide.

FIG. 22 is a diagrammatic elevational view illustrating the attachment of the coupler of this invention to the leg stump of the wearer of the prosthesis in accordance with this invention.

DESCRIPTION OF THE PREFERRED EMBODIMENT INTRODUCTION

The device of this invention as noted is found in two embodiments, the first designated 10, for above-the-knee junctions, seen in side elevation in FIGS. 3 and 4, and the second designated 110 for below-the-knee junctions, also seen in side elevation in FIG. 9. Both embodiments have an upper plate connected as will be described to a lower plate. In both instances the upper plate is the same, but in the above-the-knee embodiment the top surface of the lower plate is angularly disposed relative to the bottom surface. Substantially all other aspects of the two embodiments are the same.

It is also to be seen that the above-the-knee embodiment is made in mirror image pairs for attachment of left leg and right leg prostheses respectively. The release pin found in both embodiments and which is used to disconnect the coupler and the associated prosthesis from the stump of the user's leg, is positioned inwardly toward the adjacent leg for both embodiments of the invention. For the above knee unit, the extension section of the lower plate—that portion of the lower plate that extends beyond the outer edge of the upper plate—is disposed rearwardly when in use. Therefore, the device shown in FIG. 3 is understood to be for a left foot junction, since as noted the pin is not seen and the extension is facing rearwardly, here to the right.

The below knee unit is made in only one version because there is no asymmetric extension section. Note however, that since the release pin will be seen to be disposed off the diagonal or center line of the engaged plates, the position of the release pin will be slightly different when utilized on a left leg from the location utilized on a right leg. See FIG. 20.

Figure 1:
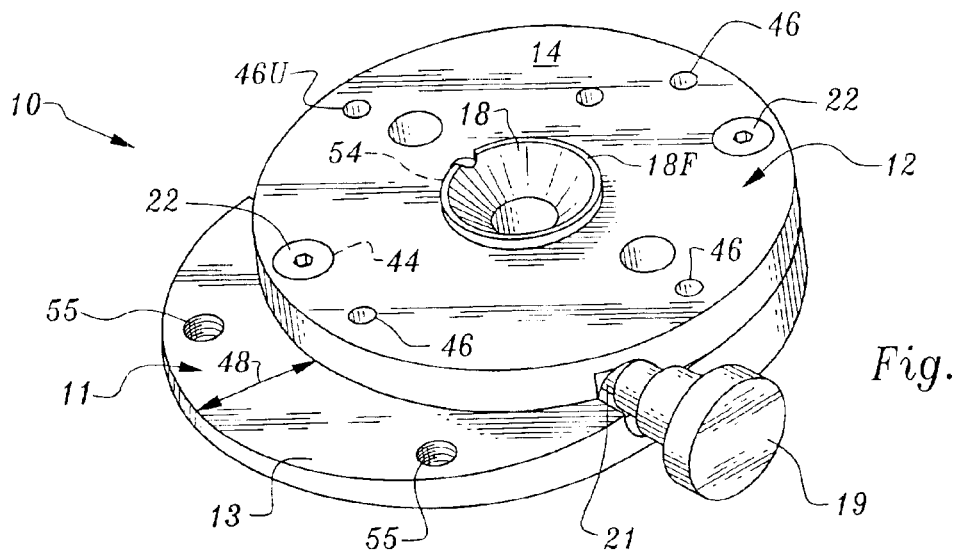
FIG. 1 is a perspective view of the above-the-knee left leg prosthesis connector of this invention. The right leg unit is a mirror image thereof.
Figure 2:
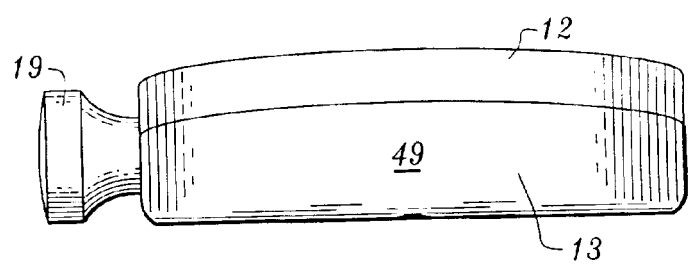
FIG. 2 is a front elevational view of the above-the-knee left leg of the prosthesis connector of this invention.
Figure 5:
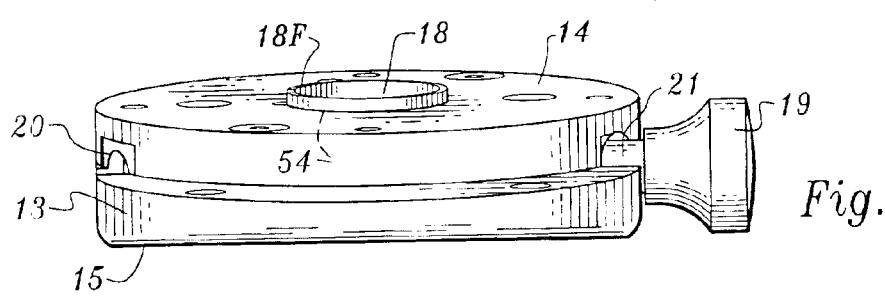
FIG. 5 is a rear elevational view thereof.
Figure 6:
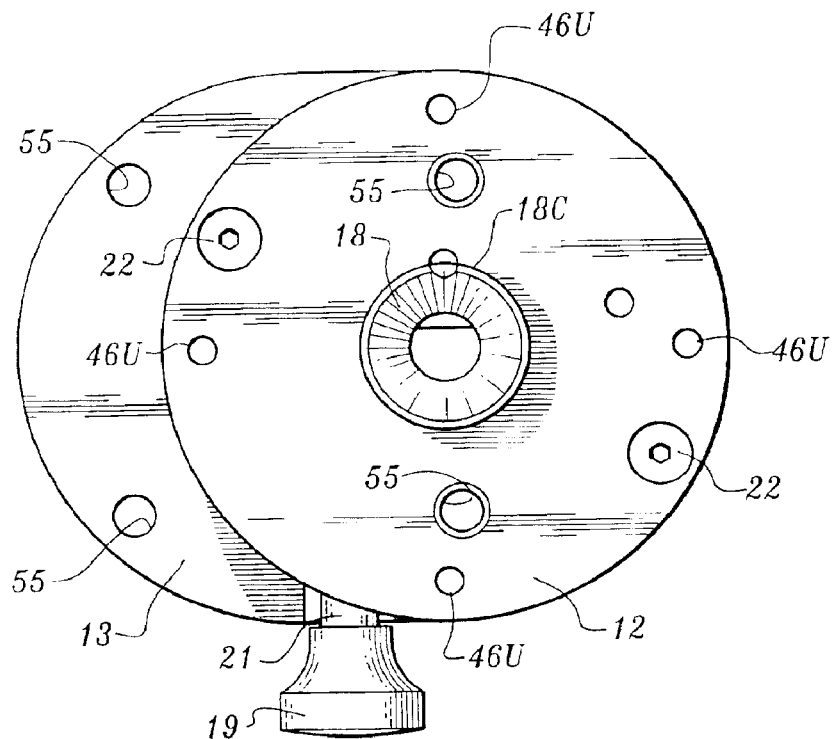
FIG. 6 is a canted auxiliary view taken along line 6—6 of FIG. 3.
Figure 7:
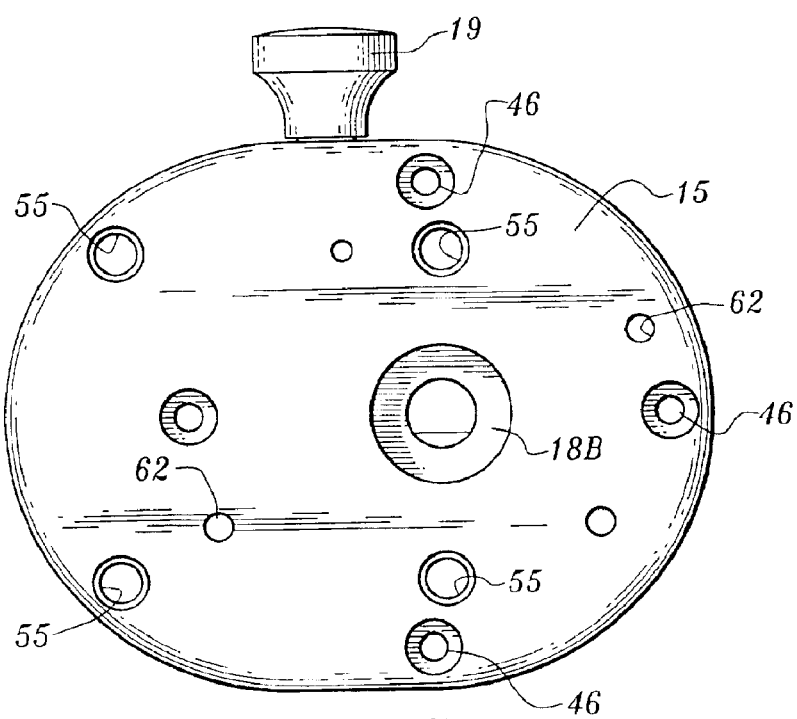
FIG. 7 is a bottom plan view of the above-the-knee connector of this invention.

The discussion now turns to FIGS. 1–7 which pertains to the above-the-knee first embodiment coupler 10 and in particular FIG. 1 to start. Lower plate 11 is seen to be a machined metal element or one of cast rigid high tolerance plastic such as of polycarbonate or Delrin®). Lower plate 11 is connected to upper plate 12 by a pair of spaced bolts 22—preferably Allen screws, through tapped bores 44 seen in FIG. 1. These bores 44 communicate through the upper plate 12 to the lower plate 11 to threaded bores 62. As seen in FIG. 7, for the aligned combination to be designated 44/62 to receive the aforementioned Allen screws 22, to mate the upper plate to the lower plate. The shaft tip of the bolts 22 are not seen in FIG. 7 since they do not consume all of the threads available, and are thus recessed inwardly. Spaced bores 46U attaches the engaged upper plate 12, to a cup-shaped pin guide such as 50 shown in FIG. 22 from the bottom surface 16 of the upper plate 12, by using recessed screws directed upwardly. Should it be necessary to remove these unseen screws, they can be accessed by placing a screwdriver through the aligned bores 46L of the lower plate 11 to the screws disposed in upper plate 12.

A concave top surface center busing 18 which receives the locking stud 40, which is also designated a shuttle pin in the industry, is press fit into the opening 54. If desired a small section of the top edge 18 may be removed as shown in FIG. 6. This little cutout 18C which may or may not constitute a throughbore, is utilized as an alignment groove of the stud receiver 18, which has a small bore thereon for insertion into this opening 54.

The angle of the incline of lower plate 11's top surface 13 is 4.5-degrees relative to the bottom surface thereof 15, per FIGS. 5, 7. Handle 19, which is attached to shaft/through pin 21 by press fit not seen, serves as the actuator button to unlock the locking stud from actual engagement with the internal mechanism to be discussed infra and seen in FIG. 16.

The shaft 21 seen in FIG. 1 and else where has a counterbore through the shaft. See FIGS. 18 and 19. The shaft 21 also includes a tapered cutaway front edge. The reasons for both of these conditions will be recited infra.

Threaded bores 55 are used to receive bolts/screws not seen for attachment to the actual prosthesis.

Figure 3:
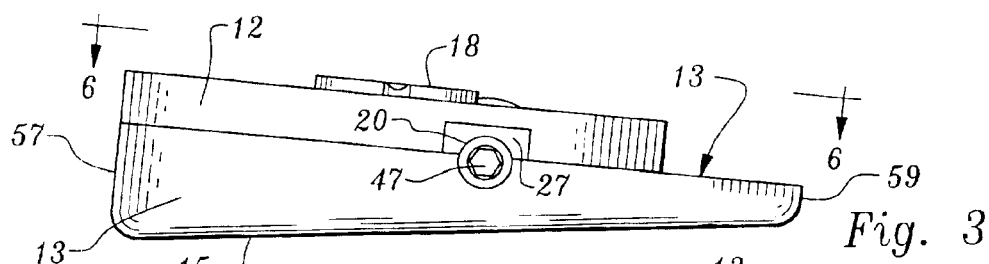
FIG. 3 is a left elevational view of the above-the-knee connector of this invention.

The base or lower plate 11 has a bottom surface 15, per FIG. 3 and a raised area 27 that engages an arch recess 20. See also FIG. 8. Within this raised area 27 is a set of bore forming threads 47 adapted to receive an Allen screw 25, this spring as noted elsewhere, holds spring 26 that engages the locking bar.

Returning to FIG. 1, top plate 12 has an upper surface 14 (FIG. 4) and a lower surface 16. Seen in FIG. 1 but not in FIG. 4, and bolts 22 connect the upper plate 12 to the lower plate 11. Openings 46 and specifically 46U have also been discussed.

The arch 20 is sized to matingly receive the raised area 27, both of which are shown in FIG. 3. See also FIG. 8.

It is seen, from FIGS. 1, 3, and 5, that bushing 18 with its rim or flange 18F while disposed in opening 54 has the rim 18F resting on top surface 14 of upper plate 12.

Figure 4:
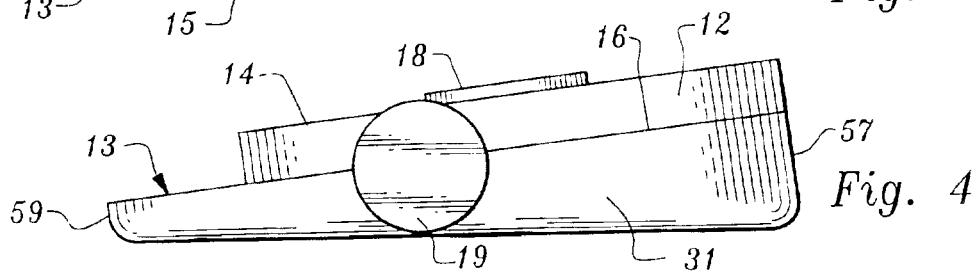
FIG. 4 is a right elevational view of the above-the-knee connector of this invention.

As can be seen from an inspection FIGS. 3 & 4, the rear wall 59 and the front wall 57 of the lower plate are of two different elevations, and both are angled relative to the base or bottom wall 15 thereof. The elevational front wall 57 is about ½ inch while the rear wall is about ⅜ inch in elevation. The front wall is disposed at an angle of about 3 degrees and the rear wall at an angle of about 3 degrees. The sidewall 31 of lower plate 11 however is generally vertical.

Also seen in FIG. 1 flange 18F of the concave stud receiver 18. This flange overlies opening 54 in the upper plate 12.

In FIG. 1, a pair of arms 48 is used to denote the distance between the rear edge of each of the upper and lower plates 14 and 11 respectively. This distance 48 is found in the upper surface 13 of lower plate 11.

FIG. 6 is a view taken along the line 6—6 of FIG. 3. Thus while FIG. 6 appears to be a top plan view. It is in fact a view taken from an angle that simulates a top plan view due to the front and rear walls of lower plate 11 being inclined. See also FIG. 3.

Bores 46 of which several are shown in FIG. 7 each receives a bolt 22 shown in FIG. 6 to secure the lower plate to the upper plate.

The reader is again reminded that the first embodiment as seen in FIGS. 1–7 pertains to a coupler for use in an above-the-knee junction for the left foot since the handle 19 points inwardly and the top wall 13 of the lower plate is to be rearwardly disposed. Threaded mounting holes 55 is used for attachment to the prosthesis.

The discussion now moves to the second or below-the-knee embodiment. In FIG. 8, a top plan view of the second embodiment is shown. As is seen from FIGS. 8 & 9, the upper and lower plates are coextensive, contrary to the first embodiment.

A quick viewing of the second embodiment as seen in a true top plan view, reveals that the elements of the top plate are the same in this embodiment as in the first embodiment of this invention. A series of bolts connects the upper plate 112 to lower concentric plate 111.

Since the upper plate is the same for both embodiments, no further discussion of element 112 need be recited at this time.

The discussion now references FIG. 10 a bottom perspective view of the lower plate of the second embodiment. In this view the lower plate 111 is seen separated from the upper plate 12. The aspects to be discussed of the operating mechanism fully apply to the mechanism found in the lower plate 11 of the first embodiment as well. The only distinction between the first and second embodiments is in the shape of the plate itself. The locking operation is the same in both embodiments.

Lower plate 111 has a top surface 113, and a side elevation 131 that are uniform circumferentially. The lower plate 111 includes two spaced and aligned hollowed out (tapped) areas having mirror right angles at the upper corners. These are designated 36 for the smaller and 35 for the larger one. The larger built-up tapped over 35 has a top slot 38 thereon to secure a pin through pin 21 per FIG. 11.

The four spaced bolt holes 37 are threaded and form an industry standard pattern in that these 6 mm bores serve to provide an attachment point for the prosthesis. This is designated as a Euro 0.4 hole pattern.

Elongated slot 288 runs normal to bore 37 and slot 38 in-between the two built-up areas 36 & 35. Disposed in slot 288 and moveable therein, guillotine 33 is held by pin 34 which allows the guillotine 33 to move as will be explained. The space 288 is the free space for the movement of the guillotine in a back and forth motion See FIG. 10.

The larger built-up area 35 includes a set of threads 47 to threadily receive the shaft of the release pin While not seen in this FIGURE, reference is made to FIG. 1. The coil spring 26 is disposed across the unused slot (free space) 288 and is retained by the shaft nut shown here. This spring impinges on the guillotine, 33, at the proximal end thereof. One end of the spring 26 may be disposed within the bore 62 (FIG. 11) to be secured by the Allen screw 25 used for limiting the movement of the guillotine 33. One merely rotates the spring in the position onto the Allen screw 25. See also FIG. 12.

Bore 24 is found in FIG. 10 and is built into larger built-up area 35. This area 35 is smooth and has no threads.

The discussion again references FIGS. 11 and 12. Whereas FIG. 10 was a perspective view while FIGS. 11 and 12 are top plan only. At the far right side of FIG. 11, the reader sees the bore pattern 37. Here in this view, the handle 19, is seen connected to shaft 21 which in turn extends through the built-up areas 35 & 36. The guillotine 33 sits in the slot 288 but only free space 288 remains empty as is shown. Note the cutaway area 66 on the guillotine 33 adjacent the central opening 54.

While the guillotine as shown is not under tension both in FIGS. 10 & 11, this position would be the engaged position if the shuttle pin were in the views. Contrast FIGS. 10, 11 with FIG. 12 wherein the coil spring is under compression due to the pressure on the shaft from the handle 19 being translated. When the handle is pushed in, as by the pressure of the thumb 200 of FIG. 12, the shaft moves; hits the guillotine, and comprises the coil spring.

Compare the position in FIGS. 11 & 12 of handle 19, shaft 21, coil spring 26 and guillotine 33. Note that pin 34 stays stationary, while the guillotine 33 moves to occupy free space 288 in FIG. 12.

Central opening 54 is where the shuttle pin would enter for engagement with the guillotine. The guillotine 33 in FIG. 11 is seen to have a removed or cutaway area 66 and a feathered edge 67 that comes in contact with the shuttle pin's groove. Allen screw 25 seen best in FIG. 12 applies pressure on the coil spring that in turn urges the guillotine toward the shaft of the release pin to return the guillotine to its original at rest position. Again contrast FIGS. 11 and 12 with respect to the position of the guillotine 33.

FIGS. 13 and 14 illustrate the underside of the upper plate 12. Here the locking stud/shuttle pin 40; which is not a part of this invention, is seen with its two types of grooves 42,43. The area 20 of the top plate 12, receives the built-up areas from the lower plate, which areas have been discussed previously. The underside of the stud receiver 18 (FIG. 1) is seen in this figure as well. It, 18 is a cylinder with a cutout 18C, seen also in FIG. 15, for the guillotine to make contact with the shuttle pin 40 through the cutout 18C of this cylindrical piece.

In FIG. 14, the elevational view of the upper plate of both embodiments the concentric non-connected grooves 43 can be readily discerned in the lower portion of the stud. The upper portion of the stud 40 has standard helical screw thread section 42. The arch configuration aspect 20 in the side wall of this upper plate 12 can be seen also. As mentioned above, this is the location for the mating with the built up area of the lower plate, of one of the two embodiments.

The elements and their numerical descriptors noted in FIG. 15 have all been discussed previously with respect to the top plate. The pin guide 50, whose underside is designated 53 forms no part of this invention. It is a prior art unit, whose presence in this view is merely to show the location of the four bores which align with apertures 46U for attachment of this pin guide or any other pin guide. A raised ridge 41 seen here, acts a separator for the two types of threads on the locking stud 40. (See also FIG. 17). When these two units are engaged, the appearance is that as depicted in FIG. 16 with the top plate overlaid on the pin guide.

In FIG. 17, the prior art cup shaped pin guide 50 is illustrated in use with the second embodiment and more specifically with the lower plate 113 thereof, which is also seen in FIG. 12. The threaded bores 39 discussed in connection with FIG. 10 only one bore 39 is seen here. These serve for access to the screws that connect the pin guide to the upper plate from the underside of the upper plate. In the first embodiment these apertures were referred to as bores 46L. Also in the figure the configuration of the Allen screw 25 is readily recognized.

In FIG. 18 the handle 19 and the shaft 21 to which it is attached are shown almost entirely withdrawn from the built up area. This was done to illustrate the presence of cross bore 29 whose purpose is secure drift pin 138 in slot 38, per FIG. 11. This shaft which moves the guillotine is also illustrated separately in FIG. 19. A cutaway area is found on the tip of the shaft and is designated 30 per this Figure. The purpose of the cutaway area is to give clearance for movement of the guillotine. As to the pin guide itself, this prior art unit 50 has a sidewall 52 and a top concave surface 51. In this FIGURE and in FIG. 12 a recess 28 is seen to be cut into the lower plate 11, to accommodate the receipt of the specific shape of the handle 19 when pressure is exerted on the handle 19.

Figure 20:
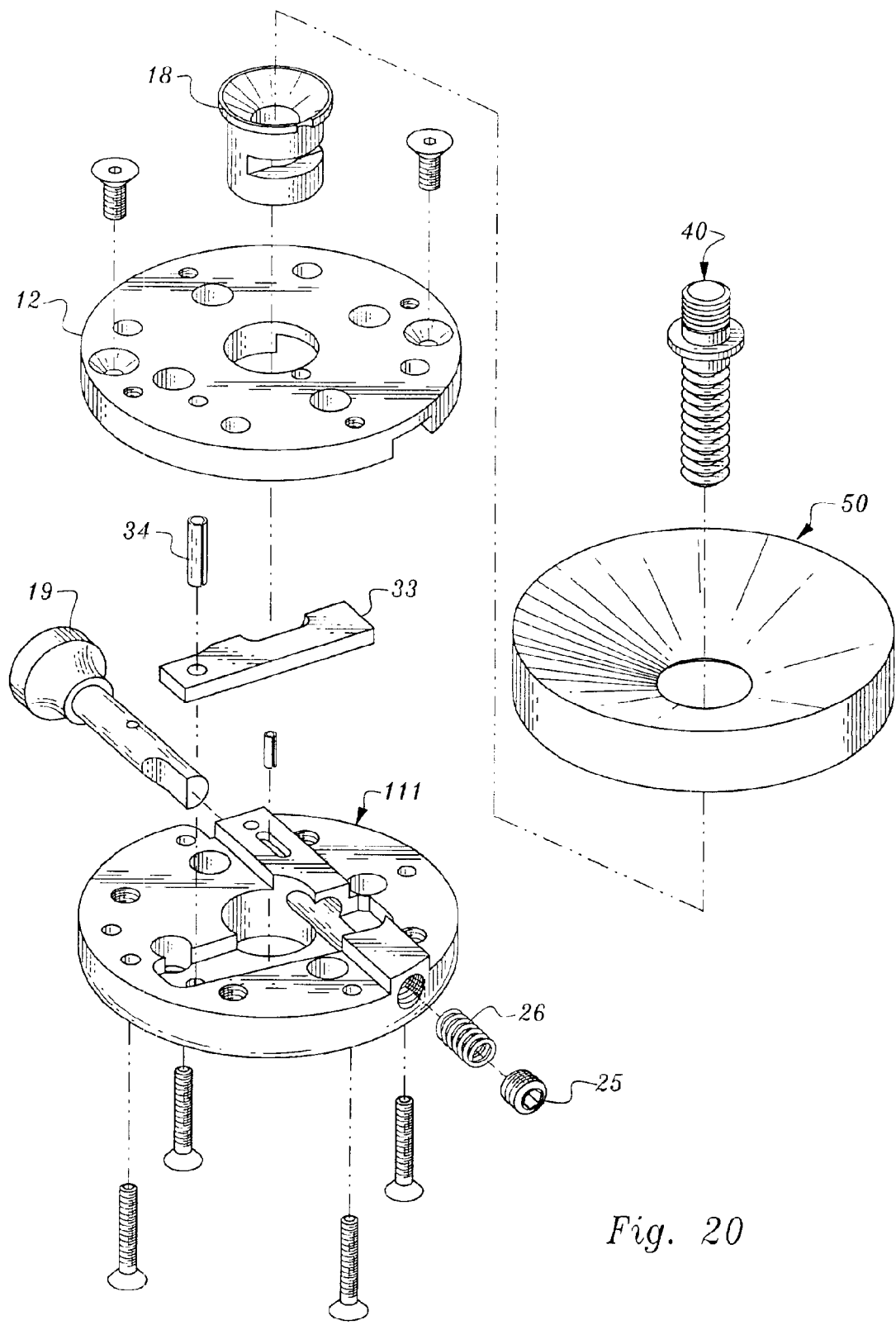
FIG. 20 is an exploded view which details the assembly of the coupler and a pin guide for utilization.

FIG. 20 is an exploded view of the second embodiment. Since the purpose of this view is merely to illustrate how the various aspects of the invention, and the pin guide which is not part of the invention interrelate and go together, the parts have been left unnumbered for ease of understanding.

USE OF THE INVENTION

FIGS. 21 and 22 illustrate the interconnection of various parts to provide prosthesis walking ability for a person. FIG. 21 provides the same information but the set up incorporates a prior art pin guide. Note however, that the two pin guides are both designated 50, since they form no part of this invention. The pin guide 50 of FIG. 22, however is the subject matter of a design application filed by this applicant, prior to the filing of this utility patent application.

In these two figures a leg stump of a human 64 is seen to disposed in a stump liner 65—conventional item found in the marketplace—and which stump liner has a T-nut 56 disposed therein to receive the conventional helical threads of the locking stud 40.

In FIG. 21 the pin passes through the pin guide 50 disposed in the interior 71 of a prosthetic socket 70 and the pin then attaches, as has been described, to one of the two embodiments, 10 or 110.

In FIG. 22, the pin guide fits directly onto the coupler of either embodiment, in the same manner as shown with respect to the discussion of FIG. 18. All other elements are the same as in FIG. 21.

It is seen that I have provided a unique coupler for use by prosthesis users, which is safe, positive locking and easy to use. In addition, this is the first coupler specifically designed for above the knee use. By making the upper plate the same for both embodiments, I have been able to keep the cost of manufacture down such that the couplers can gain wide spread usage.

The devices of this invention may be made of aluminum, or rigid, non temperature sensitive plastic such as Delrin®, nylon, polycarbonate, UHMW, tempered stainless steel, and titanium.

Other benefits of the coupler include replaceability of certain components should wear transpire. In addition, the relative simplicity of the lock gives rise to reliability of operability. One major benefit that is not apparent form the structure per se is the mechanical advantage of the release of the pin from the lock due to the nature of the design of this invention. Reference may be made to FIG. 11 wherein it is seen that hinge point 34 is on the opposite side of the hole 54 from the push release pin 21. The length of guillotine serves to increase the mechanical advantage gained upon pushing the release pin [actuator]. The analogy is the contrast of the use of a small lever versus a long lever to move a rock.

Since certain changes may be made in the described devices without departing from the scope of the invention herein involved, it is intended that all matter contained in the above description and shown in the accompanying drawings shall be interpreted as illustrative and not in a limiting sense.

I claim:

1. A coupler for releasably connecting a leg prosthetic device to a sleeve having a projecting locking stud with the sleeve configured to received the stump of a leg, said coupler comprising:

a body having a concave stud receiver disposed within a central bore of said body and retained therein, said stud receiver confining a pivotable guillotine, said locking stud having a plurality of axially spaced circumferential grooves, said stud adapted to extend into said stud receiver, which guillotine being moveable into a locking position wherein the guillotine extends into and engages one of said grooves of said stud, and a released position, retracted from said groove of said stud, in response to axial movement, and an actuator comprising a handled shaft connected to produce the axial movement of said guillotine between the engaged position with the locking stud and the released position spaced from the locking stud wherein the body is comprised of a disk shaped upper plate and an oval shaped lower plate that are engaged with each other, and the said lower plate extends out beyond the edge of the upper plate; and wherein the upper plate is disposed at a slight incline greater than 90 degrees to the lower plate.

2. The coupler of claim 1, further including means disposed on the opposite side of said guillotine from said actuator, which means includes a spring to return the guillotine to an engaged position subsequent to release caused by axial movement of the actuator.

3. The coupler of claim 2, wherein the guillotine includes a feathered edge disposed toward the interior of the central bore, which edge engages said stud.

4. The coupler of claim 1, wherein said actuator being is disposed entirely within the lower plate.

5. The coupler of claim 1, wherein the engaged plates include a set of four spaced bores for the engagement of the coupler with a pin guide.

6. The coupler of claim 1, wherein the guillotine is generally rectangular in shape, and includes an inwardly directed feather edge, said guillotine being impacted by the shaft at one end of said guillotine.

7. The coupler of claim 6, wherein the guillotine is pivoted at the end thereof, distal from the end of the point of impact of said actuator shaft.

8. A coupler for releasably connecting a leg prosthetic device to a sleeve having a projecting locking stud with the sleeve configured to received the stump of a leg, said coupler comprising:

a body having a concave stud receiver disposed within a central bore of said body and retained therein, said stud receiver confining a pivotable guillotine, said locking stud having a plurality of axially spaced circumferential grooves, said stud adapted to extend into said stud receiver, which guillotine being moveable into a locking position wherein the guillotine extends into and engages one of said grooves of said stud, and a released position, retracted from said groove of said stud, in response to axial movement, and an actuator comprising a handled shaft connected to produce the axial movement of said guillotine between the engaged position with the locking stud and the released position spaced from the locking stud wherein the body is comprised of a disk shaped upper plate and an oval shaped lower plate that are engaged with each other, and the said lower plate extends out beyond the edge of the upper plate; and wherein the lower plate includes a built up inverted U-shaped section, and the actuator shaft is disposed therein and the lower plate also includes a recess in which the guillotine is disposed.

9. The coupler of claim 8, wherein the built up section has a slot therein for the receipt of a drift pin, and said actuator shaft has a drift pin disposed normal to the axis of said shaft and which drift pin is disposed in said slot for retention of the drift pin.

10. A coupler for releasably connecting a leg prosthetic device to a sleeve having a projecting locking stud with the sleeve configured to received the stump of a leg, said coupler comprising:

a body comprising two interconnected plates, which are an upper plate and a lower plate, the upper of which is disk shaped and which overlays the lower plate, said body having a concave stud receiver disposed within a central bore of said body and retained therein, said stud receiver confining a pivotable guillotine, said locking stud having a plurality of axially spaced circumferential grooves, said stud adapted to extend into said stud receiver, which guillotine being moveable into a locking position wherein the guillotine extends into and engages one of said grooves of said stud, and a released position, retracted from said groove of said stud, in response to axial movement, and an actuator comprising a handled shaft connected to produce the axial movement of said guillotine between the engaged position with the locking stud and the released position spaced from the locking stud, further including means disposed on the opposite side of said guillotine from said actuator, which means includes a spring to return the guillotine to an engaged position subsequent to release caused by axial movement of the actuator; wherein the lower plate is oval shaped and is covered over in part by a disk shaped upper plate, the upper plate's disposition being at about a 3 degree angle.

11. A coupler for releasably connecting a leg prosthetic device to a sleeve having a projecting locking stud with the sleeve configured to received the stump of a leg, said coupler comprising:

a body comprising two engaged plates, an upper plate and a lower plate, at least the upper one of which is a disk, which body has a concave stud receiver disposed within a central bore of said body and retained therein, said stud receiver confining a pivotable generally rectangular guillotine having an inwardly directed feathered edge, said locking stud having a plurality of axially spaced circumferential grooves, said stud adapted to extend into said stud receiver, which guillotine being moveable into a locking position wherein the guillotine's feathered edge extends into and engages one of said grooves of said stud, and a released position, retracted from said groove of said stud, in response to axial movement, and an actuator comprising a normally disposed drift pin retained handled shaft to produce the axial movement of said guillotine between the engaged position with the locking stud and the released position spaced from the locking stud; wherein the lower plate includes a built up inverted U-shaped section, and the actuator shaft is disposed therein and the lower plate includes a recess in which the guillotine is disposed.

12. The coupler of claim 11, wherein the guillotine is pivoted at the end thereof, distal from the end of the point of impact of said actuator shaft.

13. The coupler of claim 12, wherein the engaged plates include a set of four spaced bores for the engagement of the coupler with a pin guide.

14. The coupler of claim 11, wherein both of said plates are disks of the same diameter.

15. The coupler of claim 11, wherein the angle of the incline of the lower plate's top surface si 4.5 degrees relative to the bottom surface thereof.

* * * * *